(12) United States Patent
Wolff

(10) Patent No.: US 6,537,974 B2
(45) Date of Patent: Mar. 25, 2003

(54) METHOD OF TREATING ARRHYTHMIAS

(75) Inventor: Andrew Wolff, San Francisco, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/949,169

(22) Filed: Sep. 7, 2001

(65) Prior Publication Data

US 2002/0055485 A1 May 9, 2002

Related U.S. Application Data

(60) Provisional application No. 60/305,328, filed on Jul. 13, 2001, and provisional application No. 60/231,011, filed on Sep. 8, 2000.

(51) Int. Cl.[7] ............... A01N 43/04; A01N 43/90; A61K 31/70; A61K 31/52; C07D 473/00
(52) U.S. Cl. ............... 514/46; 514/42; 514/43; 514/44; 514/45; 514/262.1; 514/263.1; 514/263.2; 514/263.23; 514/256; 514/257; 514/258.1; 544/262; 544/264
(58) Field of Search ............... 514/46, 261, 263, 514/264, 266; 544/262, 264

(56) References Cited

U.S. PATENT DOCUMENTS

| | | | |
|---|---|---|---|
| 4,364,922 A | * | 12/1982 | Berne et al. |
| 4,713,455 A | * | 12/1987 | Furrer et al. |
| 4,954,504 A | * | 9/1990 | Chen et al. |
| 4,980,379 A | * | 12/1990 | Belardinelli et al. |
| 5,446,046 A | | 8/1995 | Belardinelli et al. |
| 5,631,260 A | | 5/1997 | Belardinelli et al. |
| 5,736,528 A | | 4/1998 | Belardinelli et al. |
| 5,789,416 A | * | 8/1998 | Lum et al. |

FOREIGN PATENT DOCUMENTS

| | | |
|---|---|---|
| EP | 0 062 921 | 10/1982 |
| WO | WO 97/24363 | 7/1997 |
| WO | WO 98/08855 | 3/1998 |

* cited by examiner

Primary Examiner—James O. Wilson
Assistant Examiner—Traviss McIntosh
(74) Attorney, Agent, or Firm—McDonnell Boehnen Hulbert & Berghoff

(57) ABSTRACT

A method for treating arrhythmia in mammals is provided comprising administering a low dose of an adenosine receptor agonist of the Formula I:

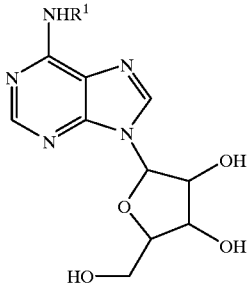

Formula I wherein $R_1$ is an optionally substituted heterocyclic group, preferably monocyclic.

11 Claims, 1 Drawing Sheet

METHOD OF TREATING ARRHYTHMIAS

This application claims the benefit of Provisional application Ser. No. 60/305,328, filed Jul. 13, 2001, and claims the benefit of Provisional application Ser. No. 60/231,011, filed Sep. 5, 2000.

BACKGROUND

1. Field of the Invention

This invention relates to a method of treating atrial arrhythmias that minimizes undesirable side effects, comprising administration of an adenosine $A_1$ receptor agonist in low doses.

2. Background Information

Atrial arrhythmias, such as primary atrial fibrillation, atrial flutter, and paroxysmal atrial tachycardia (PSVT), are abnormal heart rhythms that are due to a variety of factors. Arrhythmias can range from incidental, asymptomatic clinical findings to life-threatening abnormalities. Arrhythmias account for a significant percentage of the causes of death in human. Thus, it is desirable to develop methods of mitigating the effects of arrhythmia.

A variety of anti-arrhythmic drug therapies are presently available. These compounds, however, have significant limitations. Digoxin, for example, has a delayed onset of action (about 30 min) and its peak effects are not observed for 3 to 4 hours after administration. Other examples are β-blockers and calcium-channel blockers, which widely used to treat arrhythmias, can cause hypotension and have negative inotropic effects.

Adenosine is a naturally occurring compound that is highly effective in ameliorating arrhythmia. However, adenosine has a wide variety of physiological effects. The multiple activities of adenosine are mediated by its interactions with a family of adenosine receptors, known as the adenosine $A_1$, $A_{2A}$, $A_{2B}$, and $A_3$ receptors, each of which regulates distinct biological activites. For example, adenosine binds to adenosine $A_1$ receptors in heart resulting in a dromotrophic effect while the binding of adenosine to $A_{2A}$ results in coronary vasodilation. Likewise adenosine binds to adenosine $A_{2B}$ receptors thus affecting a wide array of activities including angiogenesis, cellular proliferation, and apopotosis, to name a few. On the other hand, adenosine binds to $A_3$ receptors on mast cells thereby stimulating degranulation and the release of histamine.

The anti-arrhythmic effects of adenosine are due exclusively to its interaction with the adenosine $A_1$ receptor subtype. However, contemporaneous binding of adenosine to the subtypes, $A_{2A}$, $A_{2B}$, and $A_3$ results in undesirable side effects, such as vasodilation, changes in the heart rate and mast cell degradation. Thus, the lack of selectivity of adenosine for the $A_1$ receptor subtype makes adenosine unsuitable for the treatment of arrhythmias. Additionally, adenosine has a short half-life (~10 sec) making it ineffective in any condition that requires prolonged drug action.

Thus, there is a need for a method of treating arrhythmias with therapeutic agents that are selective for the adenosine $A_1$ receptor, have sufficiently long half-lives, and have few side effects. Preferred compounds would be active at very low doses, since lower doses provide less opportunity for side effects.

New classes of agonists that bind to adenosine $A_1$ receptors and that are useful in treating arrhythmias are disclosed in U.S. Pat. No. 5,789,416, the entire disclosure of which is hereby incorporated by reference. These compounds have a high specificity for the adenosine $A_1$ receptor subtypes, but like all therapeutic compounds, can potentially cause side effects.

The effective dose of the compounds of '416 is disclosed to be in the range of 0.01–100 mg/kg. Surprisingly, we have discovered that the compounds are active at much lower doses (0.0003–0.009 mg/kg) than those disclosed as effective in '416. Accordingly, a novel and effective method of treating arrhythmias is provided that restores sinus rhythm without slowing the sinus rate and is virtually free of undesirable side effects, such as changes in mean arterial pressure, blood pressure, heart rate, or other adverse effects.

SUMMARY OF THE INVENTION

It is an object of this invention to provide an effective method of treating atrial arrhythmias in a mammal while minimizing undesirable side effects. Accordingly, in a first aspect, the invention relates to a method of treating atrial arrhythmias in a mammal comprising administration of a therapeutically minimal dose of an adenosine $A_1$ receptor agonist of Formula I to a mammal in need thereof:

Formula I

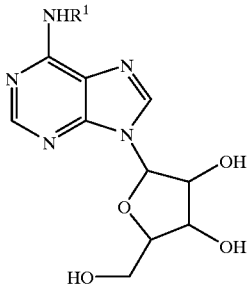

Wherein:
$R_1$ is an optionally substituted heterocyclic group, preferably monocyclic; and said minimal dose is in the range of 0.0003–0.009 mg/kg.

In a more preferred embodiment, $R_1$ is 3-tetrahydrofuranyl, 3-tetrahydrothiofuranyl, 4-pyranyl and 4-thiopyranyl.

The compounds of Formula I exist as a racemic mixture, or as individual isomers. Most preferred is 6-(3-(R)-aminotetrahydrofuranyl) purine riboside.

The most preferred embodiment of the invention is a method of treating atrial arrhythmias in a mammal comprising administering a therapeutically minimal dose of 0.0003–0.009 mg/kg of 6-(3-(R)-N-aminotetrahydrofuranyl) purine riboside, hereafter referred to as CVT-510.

Figure 1:
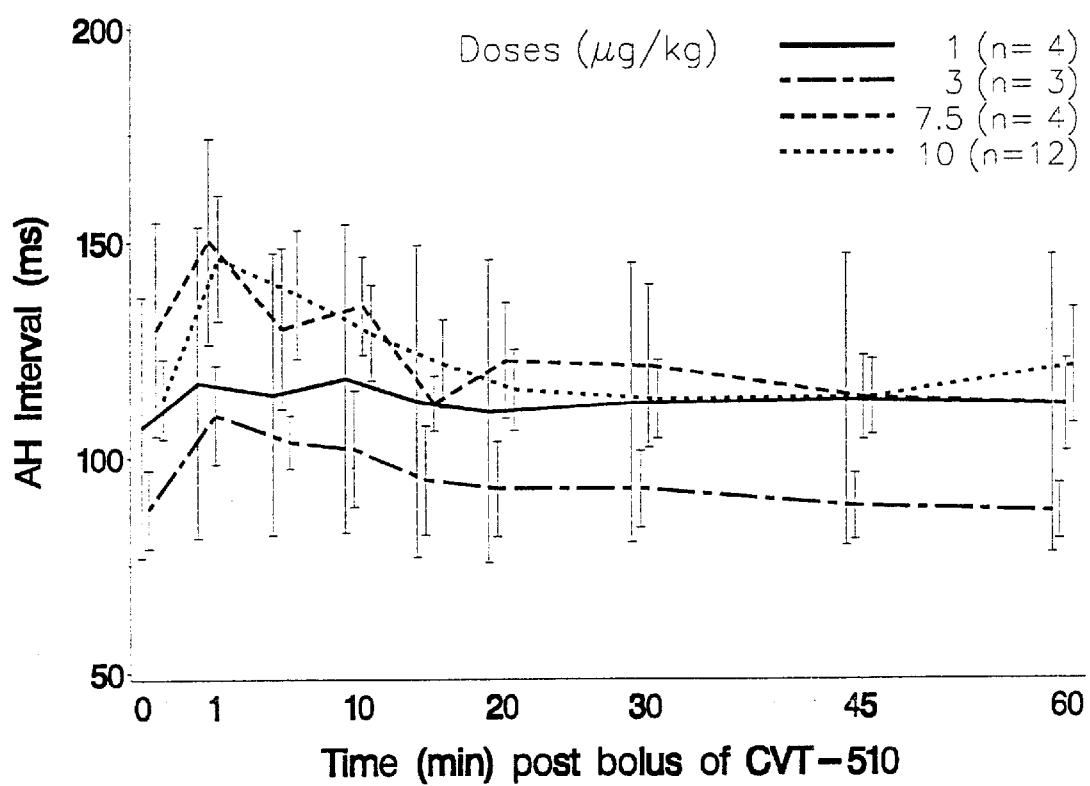
FIG. 1. Time course of the effect of CVT-510 effect on AH interval.

Table 1. The effects of CVT-510 at doses of 0.3, 1.0, 3.0, 7.5 10, 15 and 30 μg/kg on PSVT

ABBREVIATIONS:

AV: Atrial-ventricular
BP: Blood Pressure
HR: Heart rate
HV: His Ventricular
WCL: Wenckebach cycle length SH: Stimulus to His (length of time for conduction of current through AV node)

PSVT Paroxysmal Atrial Tachycardia

Definitions

As used in the present specification, the following words and phrases are generally intended to have the meanings as set forth below, except to the extent that the context in which they are used indicates otherwise.

The term "heterocycle" or "heterocyclyl" refers to a monoradical saturated group having a single ring or multiple condensed rings, having from 1 to 40 carbon atoms and from 1 to 10 heteroatoms, preferably 1 to 4 heteroatoms, selected from nitrogen, sulfur, phosphorus, and/or oxygen within the ring. Heterocyclic groups can have a single ring or multiple condensed rings. Preferred heterocyclics include tetrahydrofuran, tetrahydrothiofuranyl, pyranyl, 4-thiopyranyl, morpholino, piperidinyl, and the like.

Unless otherwise constrained by the definition for the heterocyclic substituent, such heterocyclic groups can be optionally substituted with 1 to 5, and preferably 1 to 3 substituents, selected from the group consisting of alkyl, alkoxy, cycloalkyl, acyl, acylamino, acyloxy, amino, substituted amino, cyano, halogen, hydroxyl, oxo, thioketo, carboxyl, carboxylalkyl, thiol, thioalkoxy, aryl, aryloxy, heteroaryl, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halogen" refers to fluorine, bromine, chlorine, and iodine atoms.

The term "oxo" refers to =O.

The term "hydroxyl" refers to the group —OH.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above substituted by one or more groups chosen from hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, and cyano. These groups may be attached to any carbon atom of the lower alkyl moiety.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, and the like.

The term "substituted cycloalkyl" refers to cycloalkyl groups having from 1 to 5 substituents, and preferably 1 to 3 substituents, selected from the group consisting of alkoxy, cycloalkyl, acyl, acylamino, acyloxy, amino, substituted amino, cyano, halogen, hydroxyl, keto, thioketo, carboxyl, carboxylalkyl, thiol, thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-substituted alkyl, —SO$_2$-aryl and —SO$_2$-heteroaryl.

The term "alkoxy" refers to the group —OR, where R is alkyl, lower alkyl or substituted lower alkyl as defined above.

The term "acyl" denotes groups —C(O)R, where R is hydrogen, lower alkyl, substituted lower alkyl, aryl, substituted aryl, amino, and the like.

The term "amino" refers to the group —NH$_2$.

The term "substituted amino refers to the group —NRR where each R is independently selected from the group consisting of hydrogen, alkyl, cycloalkyl, aryl, heteroaryl and heterocyclyl, provided that both R's are not hydrogen. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

The term "substituted aryl" refers to aryl optionally substituted with one or more functional groups, e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido, and the like.

The term "aryloxy" denotes groups —OAr, where Ar is aryl, substituted aryl, heteroaryl, or substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring, which may be optionally substituted with halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, or sulfamido.

The compositions of this invention are A$_1$ receptor agonists, useful for the treatment of coronary electrical disorders such as arrhythmia, including PSVT atrial fibrillation, atrial flutter, and AV nodal re-entrant tachycardia. The compositions may be administered orally, intravenously, through the epidermis or by any other means known in the art for administering a therapeutic agent.

The method of treatment comprises the administration of an effective quantity of the chosen compound, preferably dispersed in a pharmaceutical carrier. Dosage units of the active ingredient are selected from the range of 0.0003–0.009 mg/kg, dependent upon the route of administration, and the age and condition of the patient. These dosage units may be administered one to ten times daily for acute or chronic disorders.

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methane sulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as Na$^+$, K$^+$, Ca$^{+2}$ and NH$_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention. Alternatively, the compounds of Formula I may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples that follow serve to illustrate this invention. The Examples are intended to in no way limit the scope of this invention, but are provided to show how to make and use the compounds of this invention. In the Examples, all temperatures are in degrees Centigrade.

EXAMPLES

The compounds of Formula I may be prepared by conventional methods, in the manner disclosed in U.S. Pat. No. 5,789,416, the entire disclosure of which is hereby incorporated by reference.

Example 1

A. Preparation of (3-(S)-aminotetrahydrofuranyl) purine riboside

Step 1. Resolution of 3-(S)-aminotetrahydrofuran

A mixture of 3-aminotetrahydrofuran hydrochloride (0.5 GM, 4 mmol) and (S)-(+)-10-camphorsulfonyl chloride (1.1 gm, 4.4 mmol) in pyridine (10 ml) was stirred for 4 hours at room temperature and then concentrated. The residue was dissolved in EtOAc and washed with 0.5N HCl, sodium bicarbonate and brine. The organic layer was dried over $MgSO_4$, filtered, and concentrated to give 1.17 g of a brown oil (97%) which was chromatographed on silica gel (25% to 70% EtOAc/Hex). The white solid obtained was repeatedly recrystallized from acetone until an enhancement of greater than 90% by 1H NMR was achieved, to yield the (S)-camphorsulfonate of. 3-(S)-aminotetrahydrofuran.

Step 2. Preparation of 3-(S)-aminotetrahydrofuran hydrochloride

The (S)-camphorsulfonate of. 3-(S)-aminotetrahydrofuran (170 mg, 0.56 mmol) was dissolved in conc. HCl/AcOH (2 mL each), stirred for 20 hours at room temperature, washed three times with $CH_2Cl_2$ (10 ml) and concentrated to dryness to give 75 mg of 3-(S)-aminotetrahydrofuran, as a white solid.

Step 3. Preparation of 6-(3-(S)-aminotetrahydrofuranyl) purine riboside

A mixture of 6-chloropurine riboside (30 mg, 0.10 mmol), 3-(S)-aminotetrahydrofuran hydrochloride (19 mg, 0.15 mmol) and triethylamine (45 ml, 0.32 mmol) in methanol (0.5 ml) was heated to 80° C. for 18 hours. The mixture was cooled, concentrated and chromatographed with 95/5 ($CH_2Cl_2$/MeOH) to give 8 mg (24%) of 6-(3-(S)-aminotetrahydrofuranyl)purine riboside as a white solid.

B. Preparation of 6-(3-(R)-aminotetrahydrofuranyl)purine Riboside (CVT-510)

Similarly, following steps 1–3 above, but replacing (S)-(+)-O-camphorsulfonyl chloride with (R)-(-)-10-camphorsulfonyl chloride, the following compound was prepared: 6-(3-(R)-aminotetrahydrofuranyl)purine riboside (CVT-510)

Similarly, other enantiomers of the compounds of Formula are prepared.

Example 2

The effect of CVT-510 on prolongation of AH interval, a measure of an adenosine $A_1$ mediated effect of CVT-510, and on the heart rate (sinus rate) of patients with PSVT was tested in patients undergoing a clinically indicated electrophysiology study. In the first study patients volunteers were administered a single bolus of. CVT-510. In the second study PSVT was induced in patients prior to the administration of CVT-510.

All antiarrhythmic agents, including digoxin, beta-blockers and calcium-channel blockers were discontinued for five half-lives prior to the study.

Patients were excluded from the study if the PR interval was >200 ms or resting heart rate was <60 or >100/min. Other exclusion criteria included evidence of ventricular preexcitation, Class II-IV congestive heart failure or asthma. Patients were also required to have normal baseline electrophysiologic parameters, including a paced AV nodal Wenckebach cycle length 500 ms, an AH interval between 60 and 125 ms and an HV interval 35–55 ms. All patients were 18 years of age.

Quadripolar catheters were introduced percutaneously and advanced under fluoroscopic guidance to the high right atrium and across the tricuspid annulus to record the His bundle potential. Bipolar intracardiac recordings were filtered at 30 to 500 Hz and displayed with surface ECG leads on a digital monitor. Data were stored on optical disk. All patients had continuous ECG and non-invasive blood pressure monitoring throughout the study.

Cardiac stimulation was performed with a programmable stimulator with an isolated constant-current source. Stimuli were delivered as rectangular pulses of 2 ms duration at four times diastolic threshold. The study design was open-label with dose escalation, with the latter determined by tolerability. A single intravenous bolus of CVT-510 was administered to each patient after baseline electrophysiologic measurements were made.

After a bolus dose of CVT-510 was given, blood pressure, heart rate, 12-lead ECG and AH and HV intervals were recorded at 1, 5, 10, 15, 20 and 30 min and then every 15 min for up to 1 hour post-bolus or until the parameters returned to baseline. The AH and HV intervals were determined by measuring the last interval during a 15 beat drive at a paced cycle length of 600, 500 and 400 ms (unless precluded by pacing-induced AV nodal Wenckebach).

Administration of CVT-510 started at a dose of 0.3 μg/kg. Dose escalation proceeded with additional groups of patients receiving doses of 1, 3, 7.5, 10, 15 and 30 μg/kg based on tolerability and the absence of AV nodal Wenckebach or 3° AV block during sinus rhythm.

Data are expressed as mean ±SD. Based on the results of the normality test, a paired t-test or a non-parametric signed-rank test (SR) was used to determine the significance of CVT-510's effects on heart rate, blood pressure, ECG and AV nodal conduction times (AH and HV) for each dosing group (e.g., 0.3, 1.0, 3.0, 7.5, 10.0, 15.0 and 30.0 μg/kg). Similarly, analysis of variance (ANOVA) or the Kruskal-Wallis test (KW) was used to compare the AH intervals during sinus rhythm and atrial pacing at all doses. No adjustment for multiple comparisons were made, and a P value <0.05 were used to determine the significance of the differences between mean values.

The results are summarized as follows:

FIG. 1 shows the timecourse of the effect of various doses of CVT-510 on the AH interval wherein n- to the number of human patients in each group. The maximal effect of CVT-510 on the AH interval occurred one minute after dosing at a dose of 7.5 μg/kg.

TABLE 1 below shows the results of treatment of patients with PSVT with doses of CVT-510 ranging between 0.003 μg/kg–0.015 μg/kg, administered as a bolus, at least one minute apart, until the arrhythmia was terminated. Most patients (75%–100%, mean 98%) converted to sinus rhythm after the first bolus of CVT-510.

| Dose Level | % conversion after Bolus 1 | % conversion after Bolus 2 | % cumulative conversion | 95% confidence interval |
|---|---|---|---|---|
| 3 (n = 4) | 75 | 25 | 100 | cannot be determined |
| 5 (n = 9) | 78 | 0 | 78 | 0.40    0.96 |
| 7.5 (n = 4) | 100 | 0 | 100 | cannot be determined |
| 10 (n = 5) | 90 | 0 | 90 | 0.38    1 |
| 12.5 (n = 4) | 75 | 25 | 100 | cannot be determined |
| 15 (n = 10) | 80 | 10 | 90 | 0.54    0.99 |
| ALL | 0.98 | 0.98 | 0.98 | 0.98    0.98 |

The data shows that CVT-510 slows AV nodal conduction in a dose-dependent manner. The onset of action was rapid (observed by 1 min post-administration) and its effects were mostly eliminated by 20 min. There was also no effect on sinus rate, a finding suggesting a relatively greater sensitivity of the AV node than the sinoatrial node to this $A_1$ adenosine receptor agonist.

CVT-510 also showed specificity with respect to the $A_1$ adenosine receptor, i.e., there was no effect on systemic blood pressure. The effects of CVT-510 on the AV node (but not on coronary conductance) are completely abolished by the selective $A_1$ receptor antagonist CPX. CVT-510 was also shown to have no effect on left ventricular pressure or $dpdt^{-1}$ max.

In summary, the data shows that CVT-510 has novel and unique properties that make it a useful antiarrhythmic agent for the treatment of PSVT and for control of ventricular rate during atrial fibrillation/flutter. Its selective $A_1$ agonist properties allow CVT-510 to have significant negative dromotropic effects on the AV node without causing concomitant hyoptension due to $A_2$-adenosine receptor mediated effects. Its relatively long half-life compared with adenosine, also makes it possible to sustain a beneficial therapeutic effect over a longer duration.

Also, CVT-510 at low concentrations rapidly terminates PSVT, without causing hypotension, HV prolongation, or depressing sinus or AV nodal conduction after restoring SR. Selective depression of AV nodal conduction time without hypotension indicates that a constant infusion of CVT-510 may also be useful to control ventricular rate in atrial fibrillation, even in patients with left ventricular dysfunction.

The invention now having been fully described, it will be apparent to one of ordinary skill in the art that many changes and modifications can be made thereto without departing from the spirit or scope of the appended claims.

What is claimed is:

1. A method for treating arrhythmia in a mammal, comprising administering to a mammal in need of such treatment, a therapeutically effective dose in the range of 0.0003–0.009 mg/kg of an adenosine $A_1$ receptor agonist of Formula I:

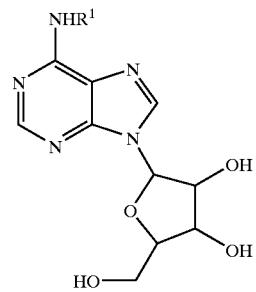

wherein $R_1$ is an optionally substituted heterocyclic group.

2. The method of claim 1, wherein $R_1$ is 3-tetrahydrofuranyl, 3-tetrahydrothiofuranyl, 4-pyranyl, or 4-thiopyranyl.

3. The method of claim 2, wherein $R_1$ is 3-tetrahydrofuranyl.

4. The method of claim 3, wherein $R_1$ is (R)-3-tetrahydrofuranyl, namely 6-(3-(R)-aminotetrahydrofuranyl)purine riboside.

5. The method of claim 4, wherein the administration is by intravenous injection.

6. The method of claim 4, wherein administration is by a single bolus.

7. The method of claim 1 where the arrhythmias are selected from the group consisting of atrial fibrillation, atrial flutter, and paroxysmal atrial tachycardia.

8. The method of claim 7, wherein $R_1$ is 3-tetrahydrofuranyl, 3-tetrahydrothiofuranyl, 4-pyranyl, or 4-thiopyranyl.

9. The method of claim 8, wherein $R_1$ is 3-tetrahydrofuranyl.

10. The method of claim 9, wherein $R_1$ is (R)-3-tetrahydrofuranyl, namely 6-(3-(R)-aminotetrahydrofuranyl)purine riboside.

11. The method of claim 1 wherein said mammal is a human.

\* \* \* \* \*